United States Patent
Matusch (10) Patent No.: US 8,394,069 B2
(45) Date of Patent: Mar. 12, 2013

(54) INJECTOR HAVING A CYLINDER-PISTON UNIT AND PERMANENTLY STERILE ACTIVE PISTON SKIRT

(75) Inventor: Rudolf Matusch, Marburg (DE)

(73) Assignee: LTS Lohmann Therapie-Systeme AG, Angernach (DE)

( * ) Notice: Subject to any disclaimer, the term of this patent is extended or adjusted under 35 U.S.C. 154(b) by 0 days.

(21) Appl. No.: 13/134,288

(22) Filed: Jun. 3, 2011

(65) Prior Publication Data

US 2011/0238015 A1 Sep. 29, 2011

Related U.S. Application Data

(63) Continuation-in-part of application No. PCT/EP2009/008611, filed on Dec. 3, 2009.

(30) Foreign Application Priority Data

Dec. 17, 2008 (DE) .......................... 10 2008 062 405

(51) Int. Cl.
A61M 5/315 (2006.01)
(52) U.S. Cl. ...................................... 604/222
(58) Field of Classification Search .................. 604/199, 604/222
See application file for complete search history.

(56) References Cited

U.S. PATENT DOCUMENTS

| | | | |
|---|---|---|---|
| 1,348,796 A | 8/1920 | Gronbech | |
| 2,902,035 A | 10/1958 | Hartley | |
| 3,016,896 A | 1/1962 | Sickle | |
| 3,946,732 A | 3/1976 | Hurscham | |
| 4,030,498 A * | 6/1977 | Tompkins | 604/152 |
| 6,174,304 B1 * | 1/2001 | Weston | 604/414 |
| 2001/0018575 A1 | 8/2001 | Lyza, Jr. | |
| 2001/0051789 A1 | 12/2001 | Parsons | |
| 2002/0013554 A1 | 1/2002 | Heinz et al. | |
| 2003/0065291 A1 | 4/2003 | Corrigan, Jr. | |
| 2009/0166978 A1 | 7/2009 | Hoffmann et al. | |
| 2010/0262125 A1 | 10/2010 | Matusch | |

FOREIGN PATENT DOCUMENTS

| | | |
|---|---|---|
| DE | 297 16 762 U1 | 6/1998 |
| DE | 102006045959 B3 * | 1/2008 |
| WO | WO 96/19252 | 6/1996 |

* cited by examiner

*Primary Examiner* — Aarti B Berdichevsky
(74) *Attorney, Agent, or Firm* — R. S. Lombard; K. Bach (57) ABSTRACT

A unidirectional injector having at least one cylinder-piston unit, the piston thereof being displaceable between two stroke end positions relative to the cylinder, wherein the cylinder-piston unit comprises at least one sealing system sealing a compensating space from the surroundings. To this end the piston is provided at its front surface with an axial annular groove for accommodating a seal ring or a permanently elastic seal material, that the cylinder is provided with a first seal element and a second seal element which are spaced by at least a piston stroke, or that the piston is provided with the first seal element and the second seal element which are spaced by at least a piston stroke, or the cylinder carries the first seal element and the piston carries the second seal element which is displaced with respect to the first by the piston stroke.

7 Claims, 5 Drawing Sheets

INJECTOR HAVING A CYLINDER-PISTON UNIT AND PERMANENTLY STERILE ACTIVE PISTON SKIRT

CROSS-REFERENCE TO RELATED APPLICATION

This is a continuation-in-part application of pending international application PCT/EP2009/008611 filed Dec. 3, 2009 and claiming the priority of German Application No. 10 2008 062 405.5 filed Dec. 17, 2008.

BACKGROUND OF THE INVENTION

The invention relates to a disposable injector having at least one cylinder-piston unit, the piston of which can move between two stroke end positions in relation to the cylinder, the cylinder-piston unit comprising at least one sealing system that seals a compensating space from the surroundings.

Such a disposable injector is known. During the transfer-pumping, germs from the air could get into the cylinder interior.

U.S. Pat. No. 4,030,498 A discloses a syringe which has two seals spaced apart on a piston rod.

WO 2008/037 329 A1 discloses a cylinder-piston unit with a cylinder and a piston which is guided therein and which is sealed off in a sterile manner by a rubber seal, wherein the cylinder and the piston enclose a chamber that can be filled at least temporarily with active substance, and the cylinder has at least one discharge element at its front end. When the piston is actuated, two individual static sealing elements are transferred from their respective sealing position into a parked position located in the parking area, wherein each sealing element in the parked position touches only the cylinder wall or only the piston wall.

The present invention is therefore based on the problem of developing a disposable injector in which the aforementioned disadvantage cannot occur.

SUMMARY OF THE INVENTION

This problem is solved by the features of the main claim, wherein
the piston (111) is provided at its front surface with an axial annular groove (112) for accommodating a seal ring (114) or a permanently elastic seal material,
that the cylinder (101) is provided with a first seal element (124) and a second seal element (125) which are spaced by at least a piston stroke, or
that the piston (111) is provided with the first seal element (124) and the second seal element (125) which are spaced by at least a piston stroke, or
the cylinder (101) carries the first seal element (124) and the piston (111) carries the second seal element (125) which is displaced with respect to the first by the piston stroke.

BRIEF DESCRIPTION OF THE DRAWINGS

Further details of the invention will become clear from the following description of illustrative embodiments represented schematically in the drawing, in which.

DETAILED DESCRIPTION OF THE PARTICULAR EMBODIMENTS

Figure 1:
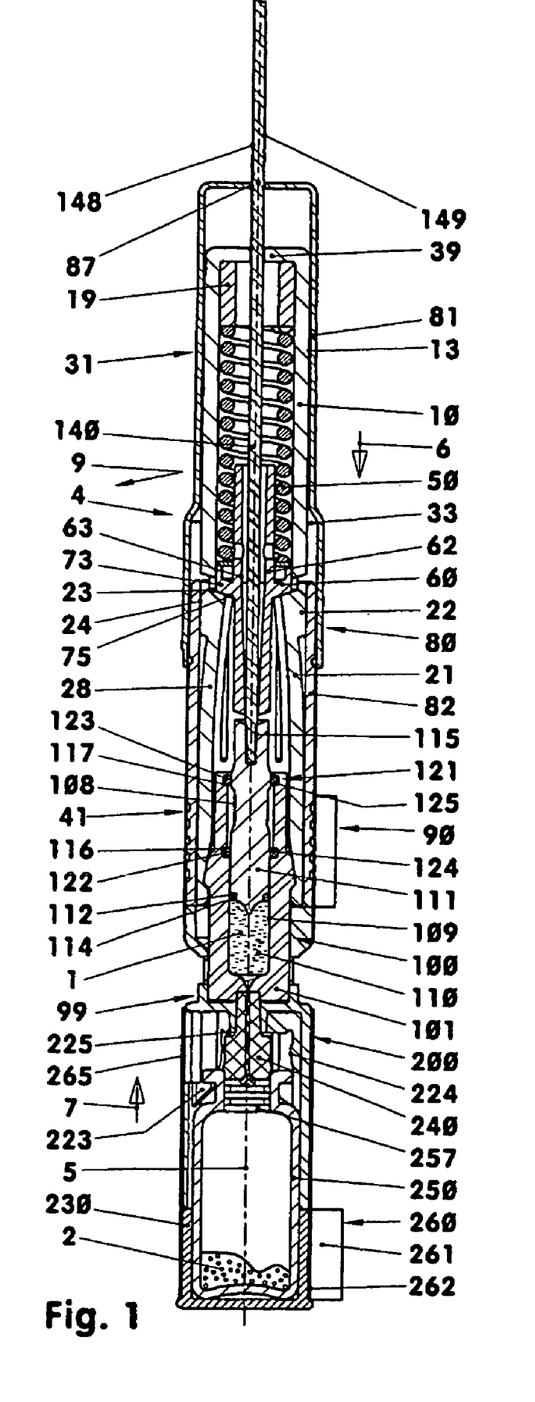
FIG. 1 shows a disposable injector having a twin-chamber system.
Figure 2:
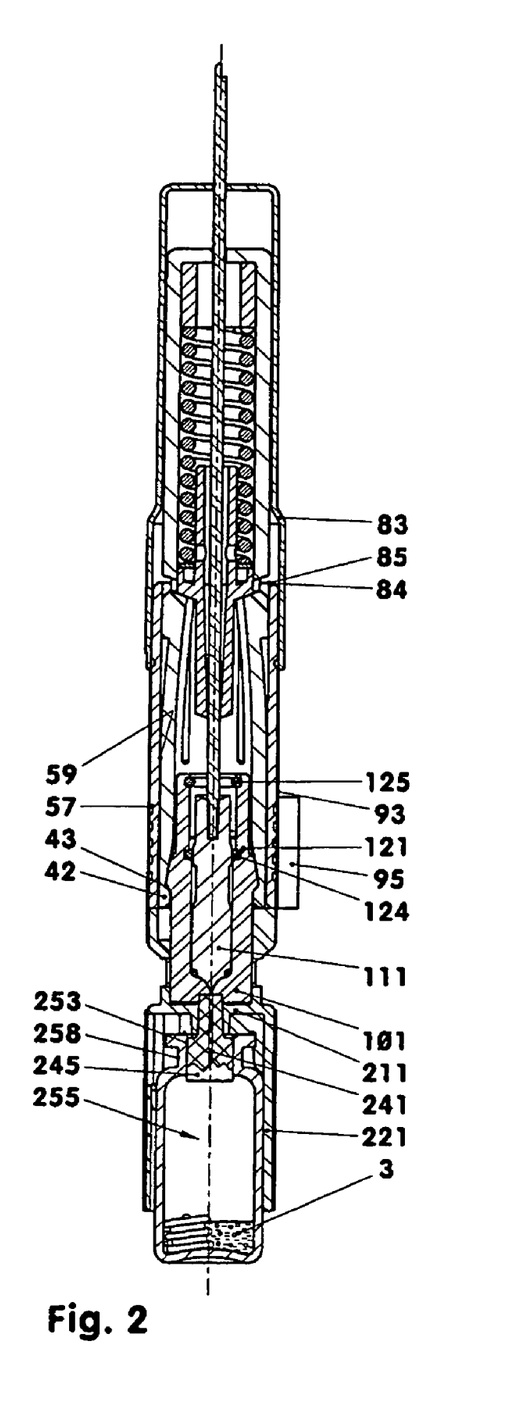
FIG. 2 shows the disposable injector after the pushing-in of the lyophilisate container and reconstitution.
Figure 3:
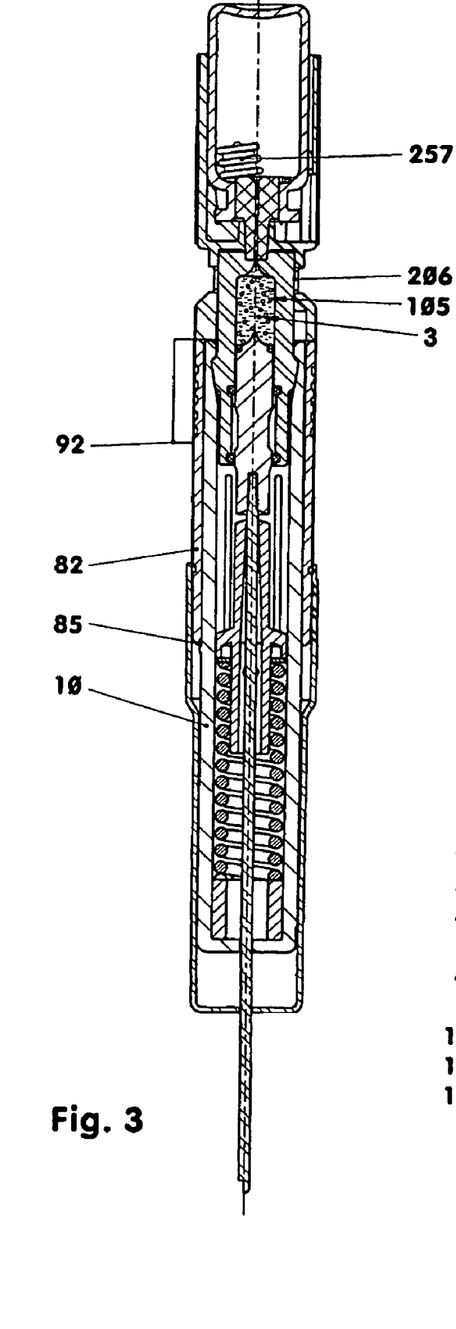
FIG. 3 shows the disposable injector after the transfer-pumping.
Figure 4:
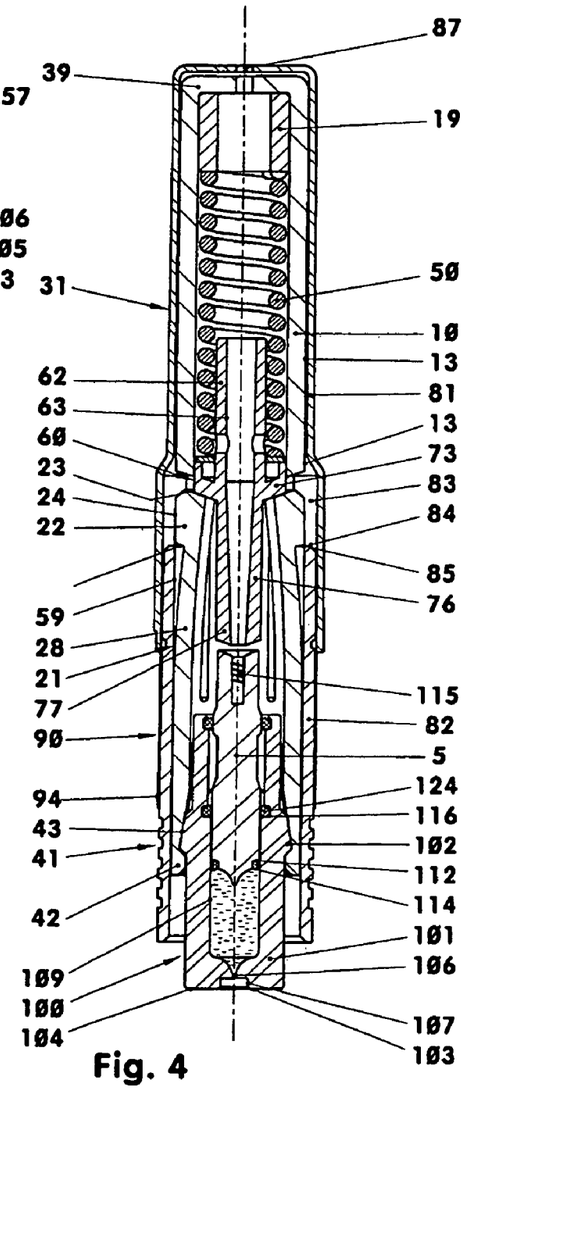
FIG. 4 shows the disposable injector with the cylinder-piston unit before the triggering.
Figure 5:
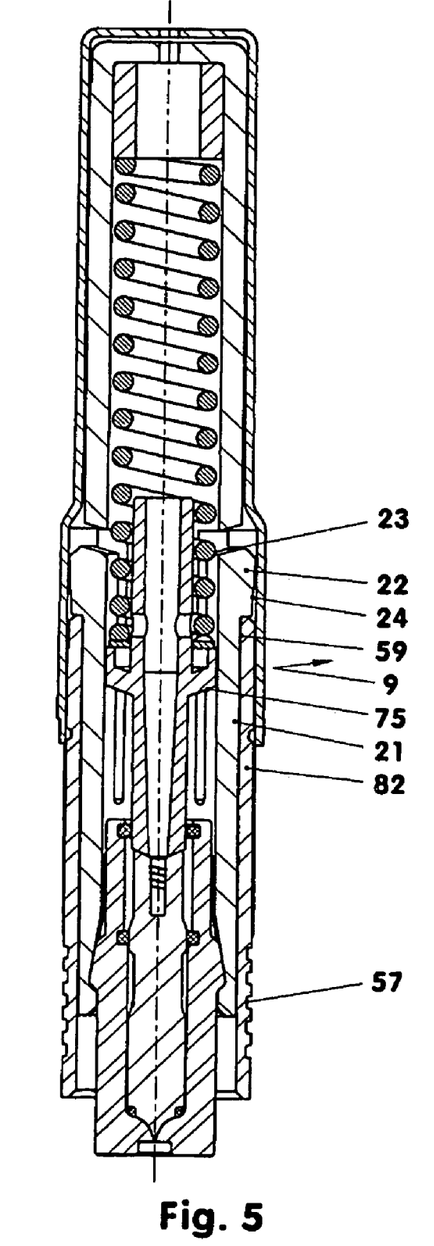
FIG. 5 shows FIG. 4 after the injection.

FIGS. 1-5 show a disposable injector (4) and a twin-chamber system (99) adapted to it. FIG. 1 shows, for example, the state on delivery to the user, in which the disposable injector (4) is pretensioned, the first chamber (105) is, for example, partially filled with solvent (1) and the second chamber (255) is, for example, partially filled with lyophilisate (2) and the two chambers (105, 255) are separated from each other. In the illustration of FIG. 2, the two chambers (105, 255) have been connected to each other and the injection solution prepared. FIG. 3 shows the disposable injector (4) and the twin-chamber system (99) after the preparation and transfer-pumping of the injection solution and FIG. 4 shows this injector (4) with the injector-side chamber (105) before the triggering. In the illustration of FIG. 5, the needleless disposable injector (4) has been triggered and the injection solution (3) injected out.

The disposable injector (4) illustrated in FIGS. 1-5 comprises a housing (10), a piston-actuating ram (60) and a helical compression spring (50) as a spring energy store. Moreover, a triggering unit (80) having a triggering element (82) and a security element (90) are arranged on the housing (10).

The housing (10) is a one-part, pot-shaped, downwardly open hollow body with a base (39) at the top. It is produced, for example, from a glassfiber reinforced polyamide by injection molding. The housing (10) has a largely tubular shape and is divided into two functional areas, on the one hand the upper lateral area (31) and on the other hand the lower fixing area (41).

In the lateral area (31), the housing (10) has, for example, two mutually opposite window-like apertures (33). On the lower edge of the individual aperture (33), a pressure rod (21) is in each case integrally formed as an elastic flexural beam. The location where the pressure rods (21) are integrally formed lies just above the fixing area (41). For the formation of the respective pressure rod (21), there is in the lower area of the lateral portion (31) a narrow, at least approximately u-shaped gap, which surrounds the individual pressure rod (21) to the sides and on top.

Along 80% of its length, for example, the pressure rod (21) has the wall thickness and curvature of the wall of the housing (10). This area also has the function, inter alia, of a resiliently elastic flexural beam (28). It has a crescent-shaped cross section.

Part of this flexural beam (28) may also be provided with a rectangular cross section, in order to reduce flexural stresses occurring in the edge region of the flexural beam during use.

The free end of the individual pressure rod (21), here the upper end, is formed by the radially outwardly protruding cam (22). The latter has at least one supporting surface (23), oriented in the direction of the center line (5), and a bearing surface (24), facing away from the center line (5).

The lower half of the housing (10) is surrounded by the sleeve-like triggering element (82). This is, for example, of a substantially cylindrical form and is produced, for example, from acrylonitrile-butadiene-styrene copolymer (ABS). The triggering element (82) is mounted so as to be movable along the radial outer surface (13) of the housing (10). It ends at the rear with a sharp edge (85), which is part of a return flank (84) at the end face of the triggering element (82). Below the edge (85), according to FIG. 1, the cams (22) formed integrally on the pressure rods (21) make secure contact with the inner wall (59) of the triggering element (82) with their outer bearing surfaces (24).

A triggering cap (81), which completely surrounds the rear end of the housing (10), is secured on the triggering element (82), for example near the edge (85). The triggering cap (81) comprises a circumferential widening (83), in which the cams (22) are received when the injector is triggered, cf. FIG. 5. Instead of this widening (83), partial widenings or uncovered openings may also be provided for each pressure rod (21) in the case of a non-rotationally symmetrical triggering element (82). Above the widening (83), the triggering cap (81) bears slidably on the outer wall (13) of the housing (10).

The piston-actuating ram (60) arranged in the housing (10) is divided into two areas. The lower area is the piston slide (76). The diameter thereof is slightly smaller than the inside diameter of the rear area of the cylinder (101) of a cylinder-piston unit (100). The lower end face (77) of the piston slide (76) acts directly on the piston (111) of this cylinder-piston unit (100). The end face (77) and the rear side of the piston facing it are, for example, of a complementary form and have at least approximately the same cone angle. In the starting position illustrated in FIG. 1, the piston slide (76) and the piston (111) are, for example, at a distance of 2-4 millimeters.

The upper area of the piston-actuating ram (60), the ram plate (73), is a flat, at last partially cylindrical disk, of which the outside diameter is several tenths of a millimeter smaller than the inside diameter of the housing (10) in the lateral area (31). The lower end face has a collar surface (75) arranged around the piston slide (76). It has the form of the lateral surface of a truncated cone of which the vertex angle is about 100 to 140 degrees. In the illustrative embodiment illustrated, the collar surface (75) has a vertex angle of 140 degrees. The imaginary vertex of the lateral surface of the truncated cone lies on the center line (5) in the area of the piston slide (76). The collar surface (75) may also be spherically curved.

The piston slide (76) may of course also be designed as a component that is separate from the ram plate (73). For this purpose, it is then guided on the inner wall of the housing (10).

The helical compression spring (50) sits pretensioned between the ram plate (73) and the base (39) lying at the top of the housing (10). The helical compression spring (50) is supported on the base (39) of the housing (10) by way of a spacer sleeve (19). The spring force of the helical compression spring (50) is transferred to the pressure rods (21) by way of the ram plate (73). On account of the inclination of the collar surface (75), the pressure rods (21) are forced radially outward in the manner of a wedge gear. The triggering sleeve (82) permanently supports this radial force.

Above the ram plate (73), the piston-actuating ram (60) has a guide pin (62). The latter guides the helical compression spring (50) or is guided by the latter. Below the ram plate (73), the piston slide (76) is located centrally in the continuation of the guide pin (62).

The fixing area (41) for receiving the insertable cylinder-piston unit (100), which comprises the first chamber (105), is located below the lateral portion (31). The fixing area (41) comprises, for example, eight spring hooks (42) oriented parallel to the center line (5). The spring hooks (42) each have an at least two-flanked rear-engagement means (43) for receiving the cylinder-piston unit (100) free of play. The mutually opposite flanks of the rear-engagement means (43) enclose an angle of 90 degrees, for example. The length and the spring rate of the spring hooks (42) are dimensioned such that the cylinder-piston unit (100) can be inserted without plastic deformation of the spring hooks (42).

In the illustrative embodiment, the cylinder-piston unit (100) is composed of a transparent cylinder (101), which can be filled with water for injection purposes (1) or an injection solution (3). The water for injection purposes (1) may already contain active substances.

The cylinder (101) is, for example, a see-through, thick-walled pot, of which the optionally cylindrical outer wall supports a, for example circumferential, locking ring (102) that bears in a dimensionally stable manner on the flanks of the rear-engagement means (43) of the spring hooks (42). The cylinder (101) is produced, for example, from the amorphous thermoplastic cyclo-olefin copolymer (COC). This material is virtually impermeable to water vapor, which makes long-term storage of the injection solution possible The rodless piston (111) sits in the, for example cylindrical or conical, bore of the cylinder (101). This piston is produced, for example, from the Teflon® derivative tetrafluoroethylene/hexafluoroethylene copolymer (FEP).

In the illustrations of FIGS. 1-5, the inner cylinder wall (109) has two annular grooves (116, 117), which are offset in relation to each other in the longitudinal direction and in which a sterile-closing sealing system (121) with two fixing areas (122, 123) is mounted. In the illustrative embodiment, the distance between the two annular grooves (116, 117) is greater than the piston stroke. The two fixing areas (122, 123) are, in the illustrative embodiment, each part of a sterile-closing sealing element (124, 125), for example, of sealing rings, which bear against the piston (111). The sealing elements (124, 125) may, however, also be quad rings, lip seals or other equivalent sealing elements. The sealing elements (124, 125) of this two-part sealing system (121) may optionally be adhesively bonded to the cylinder.

Instead of on the inner wall (109) of the cylinder (101), the fixing areas (122, 123) may be held in the piston (111). There, they are likewise spaced apart from each other by at least the piston stroke.

It is likewise conceivable to arrange a first fixing area (122) on the cylinder (101) and a second fixing area (123) on the piston (111). The two fixing areas (122, 123) can then be offset in relation to each other by the piston stroke, without the active piston skirt being able to transport germs from the surroundings (9) into the cylinder interior (110).

Figure 6:
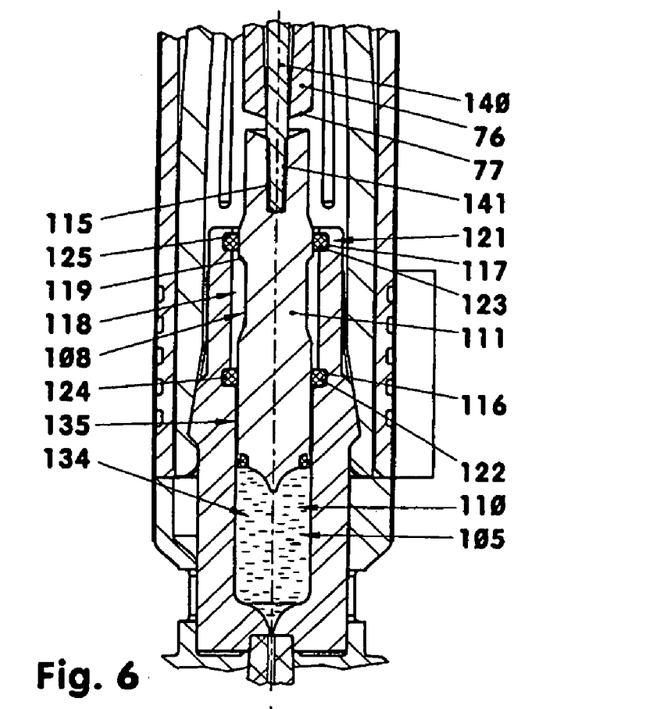
FIG. 6 shows a detail of the cylinder-piston unit with the cylinder filled.

FIG. 6 shows a detail of the disposable injector (4) shown in FIG. 1. The piston (111) sits in the, for example cylindrical, bore of the cylinder (101) in the extended stroke end position. Both sealing elements (124, 125) bear against the piston (111) and close off the cylinder interior (110) and the sealed portion (118) from the surroundings (9) in a sterile manner.

Between the two annular grooves (116, 117), the cylinder (101) is widened, so that even an unguided piston (111) cannot make contact with the cylinder (101) in this area. In the illustration of FIG. 6, the piston is narrowed in the portion (118) that is sealed in a sterile manner. The circumferentially narrowed area (108) has a length which corresponds to about 25% of the overall length of the piston. The narrowed area (108) has a diameter which is 16 to 20% smaller than the maximum inside diameter of the cylinder in the area of the solution-receiving cylinder interior (110). The front transition, which lies between the narrowed area (108) and the front, that is in this case lower, piston area, has, for example, a cone angle of 35 to 40 degrees. The other, rear transition has a cone angle of between 35 and 90 degrees. The end of the piston (111) that is the upper end in this illustration is, for example, conically formed above the sealing element (125).

At its front, at least approximately conical end face, the piston (111) has an axial annular groove (112) for receiving a sealing ring (114) or a permanently elastic sealing compound. This sealing ring (114) separates in the cylinder interior (110) a displacement space (134) from a compensating space (135). The piston (111) has on its rear side a, for example central, frustoconical-envelope-shaped recess (115) into which a pump rod (140) is screwed by means of a conical thread (141). The pump rod (140) can be released from the piston (111) with the expenditure of little force. Optionally, a, for example cylindrical, metal plate may be let into the rear end face of the piston (111) for this purpose.

For coupling onto the piston (111), the pump rod (140) has at its lower end, for example, a conical angular thread (141), a trapezoidal thread, etc. The cone angle of the angular thread (141) is, for example, six degrees. The thread turn of the angular thread (141) presses the required counter-thread into the piston recess (115) when the pump rod (140) is screwed in. The screwing-in operation is completed, for example, when the front end of the pump rod (140) comes into contact with the base of the recess (115). The special thread (141) described, used for coupling purposes, requires only low screwing-in and unscrewing forces. Other releasable couplings can of course also be used, such as for example a key/keyhole system or a simple catch system.

The pump rod (140) has, for example, a constant cross section and a smooth surface over most of its length. Its maximum diameter in the illustrative embodiment is about two millimeters. It is made, for example, of a polyamide reinforced with glass fibers. At its rear end, which protrudes from the bore (87) of the triggering cap (81), it has, for example, two differently graduated scales (148) and (149). The scale (148) is for a cylinder-piston unit (100) of which the cylinder (101) has an average inside diameter of seven millimeters, while the other scale (149) is for a cylinder (101) with an inside diameter of six millimeters. The different-sized cylinders (101) can be inserted into the injector (4) alternately.

Figure 7:
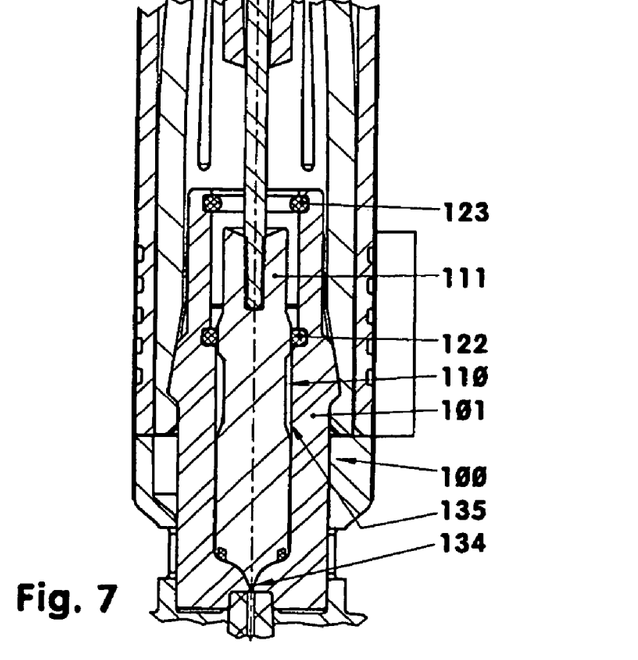
FIG. 7 shows a detail of the cylinder-piston unit with the cylinder empty.

FIGS. 2 and 7 show the piston (111) in the retracted position. The rear end of the piston (111) has left the upper sealing element (125). The upper widening (119) of the piston (111) now lies in the region of the lower sealing element (124). The sealing system (121) continues as before to seal off the cylinder interior (110) in a sterile manner.

In the center of the bore of the cylinder (101), of which the cylinder base is adapted at least approximately to the contour of the front end face of the piston, there is a short cylindrical, nozzle-like bore (106). The diameter thereof is approximately 0.1 to 0.5 millimeter. This bore (106) is one to five times as long as its diameter. It ends in a cylindrical recess (107) in the outer end face (103) at the bottom of the cylinder (101). In order to increase application safety, this end face (103) may be additionally provided with an adhesive ring (104).

The spring energy store (50) or the drive unit of the disposable injector is arranged between the piston (111) and the bottom (39).

The spring energy store (50) is a helical compression spring, which is arranged on the piston-actuating ram (60) with the ram plate (73). The piston-actuating ram (60), loaded with spring force, is supported on the pressure rods (21) of the housing (10) by means of the ram plate (73).

Above the piston (111), the piston-actuating ram (60) is arranged in the housing (10) in such a way, for example, that although not touching the piston it is guided laterally with its lower end, for example, in the upper area of the cylinder (101). The piston-actuating ram (60) has a, for example central, bore (63), through which the pump rod (140) passes with a high degree of play. The upper half of the through-bore (63) is largely cylindrical, while the lower half tapers conically downward. In the area of the lower end face (77), the bore is only one to two tenths of a millimeter larger than the outside diameter of the pump rod (140).

Below the triggering element (82) there is a container adapter (200), in which the container (250), closed with a stopper (257) and partially filled, for example, with a lyophilisate (2), is arranged. The container (250) is secured to the container adapter (200) by way of a cap (230) and a tear-off banderole (260). Between the container (250) and the cylinder (101) sits a drilled-through dual adapter (240).

For packing of the disposable injector (4) with a twin-chamber system (99), for example, the first cylinder-piston unit (100) is inserted into the disposable injector (4) and interlocked. The container adapter (200) is also inserted into the disposable injector (4). The second cylinder (250) is inserted into the container area (221) and interlocked in the locking hooks (223) facing away from the intermediate base (211). The stopper (257) is closed. After this, the tamper-evident seals (90, 260) are applied.

To be able to use the disposable injector, the active substance (2), for example the lyophilisate, which is stored in the container (250), must be dissolved in the liquid (1) present in the cylinder (101) of the cylinder-piston unit (100), for example water for injection purposes or physiological saline solution. For this purpose, the liquid (1) must be pumped into the container (250).

In a first step, the tear-off tab (261) is removed from the cap (230), while severing the perforation (262), and the cap (230) is withdrawn from the rear part of the container (250).

Optionally, an elastic sealing ring, which closes the joint between the container (250) and the inner wall of the container area (221) in a sterile manner, is located in an annular groove of the container area (221).

In a second step, the container (250) is pushed into the container adapter (200). In this case, the container (250) slides forward on the inner wall of the container adapter (200) until it bears with the flange edge (258) against the stops (225). At the same time, the locking rear-engagement means (224) reach around the rear side of the flange edge (258) and thus secure the front position of the container (250). During the forward movement, the container (250) has pressed the folding locking hooks (223) to the side and the opening (253) of the container (250) has pushed itself over the peripheral web in a sealing manner onto the container portion (245) of the dual adapter (240). In this process, the container stopper (257) has been pushed inward out of the opening (253), such that the cylinder interior (110) and the container interior (255) then communicate by way of the through-channel (241).

The overpressure that arises in the container area (221) as the container (250) is pushed in escapes via the partially lifting valve hose (265).

In a third step, the piston (111) is pushed into the cylinder (101) by means of the pump rod (140) and thus conveys the liquid (1) into the container interior (255), which is now at a slight overpressure, cf. FIG. 2. For this purpose, the pump rod (140) is generally held between the index finger and thumb of the hand operating it. As the piston (111) is pushed in, the sealed, sterile portion (118) of the piston (111) is moved into the cylinder interior (110). If germs have gathered on the piston (111) of the cylinder-piston unit (100), for example during storage, this contamination is outside the sealing element (124), and consequently outside the sealed cylinder interior (110), after the pushing-in of the piston (111), cf FIG. 7.

The lyophilisate (2) dissolves in the liquid (1). The dissolution process can be monitored visually, since the container (250) protruding from the container adapter (200) is transparent.

In a fourth step, cf. FIG. 3, the newly produced solution (3) is pumped back into the cylinder interior (110). For this purpose, the injector is held in such a way that the opening (253) of the container (250) points in the direction of gravity. The piston (111) is drawn into a rear position by the pump rod (140). Bubble-free filling is checked through the windows (206).

In a fifth step, to prime the disposable injector, the tear-off banderole (94) is separated all the way round from the main part (92) and from the adapter part (93) with the aid of the tear-off tab (95). The flutes (57) of the triggering element (82) become visible. The container adapter (200) is then pulled off downward from the cylinder (101), cf. FIG. 4.

In a last step, the injector is placed onto the injection site and the sleeve-like triggering element (82) is pushed downward—in the direction of the injection site. The pressure rods (21) bend elastically outward into their actual starting position. The cams (22) thereby slip outward over the edge (85) into the widening (83). The pressure rods (21), which are then no longer deformed, release the piston-actuating ram (60), so that the piston (111) moves abruptly downward, under the action of the spring element (50), for draining the cylinder (101), cf. FIG. 5. During the forward movement of the piston (111), the friction of the piston is reduced for a time, since the sealing elements (124, 125) do not bear against it in a slowing manner as they pass the narrowed piston area (108).

Figure 8:
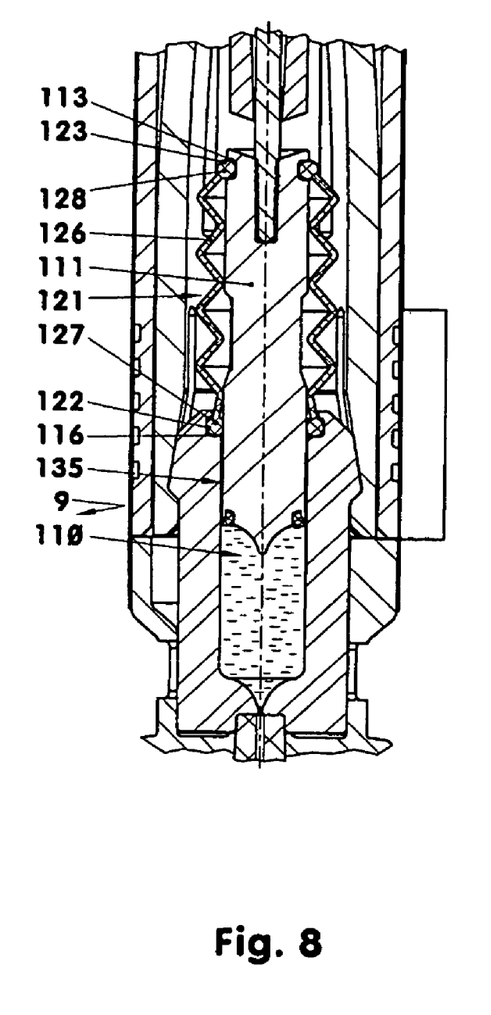
FIG. 8 shows the disposable injector with a sealing bellows when the piston is extended.
Figure 9:
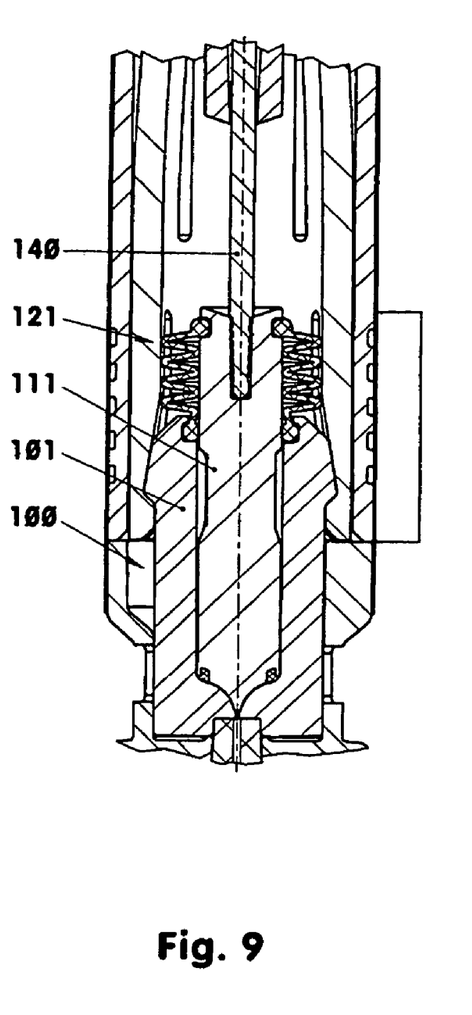
FIG. 9 shows FIG. 8 with the piston retracted.

FIGS. 8 and 9 show a disposable injector (4), the sealing system (121) of which has two fixing areas (122, 123) connected by means of a bellows (126), for example a corrugated bellows.

Both fixing areas (122, 123) are each part of elastically deformable rings (127, 128). The ring (127) that is the lower ring here sits in an annular groove (116) of the cylinder (101) and in this illustrative embodiment bears against the piston (111). The upper ring (128) sits in an annular groove (113) of the piston (111). The sealing system (121) covers the movement joint between the cylinder (101) and the piston (111), and thus hermetically seals the cylinder interior (110). The corrugated bellows is formed in the longitudinal direction of the injector (4) with such a length that the two fixing areas (122, 123) can be offset in relation to each other by at least the piston stroke. In FIG. 8, the sealing system (121) is shown with the piston (111) extended and in FIG. 9 it is shown with the piston (111) retracted. The compensating space (135), and consequently the cylinder interior (110), is sealed from the surroundings (9) in a sterile manner and protected from any contamination.

The actuation of the disposable injector (4) shown in FIGS. 8 and 9 takes place in the way described in relation to the illustrative embodiment shown in FIGS. 1-7.

Figure 10:
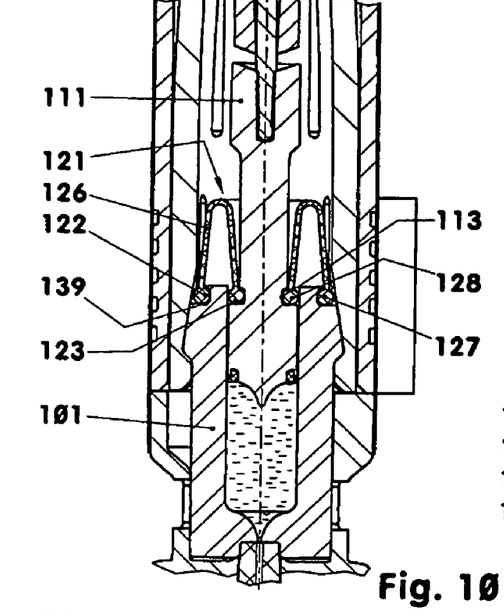
FIG. 10 shows the disposable injector with a U-type bellows.

The bellows (126) may also be formed as a U-type bellows, cf. FIG. 10. The cylinder-side fixing area (122) of the sealing system (121) may be held in an annular groove (139) on the outerside of the cylinder (101). The piston-side fixing area (123) of the sealing system (121) may, for example, enter the cylinder (101). In the illustrative embodiment, this fixing area (123) is not in contact with the cylinder (101).

Figure 11:
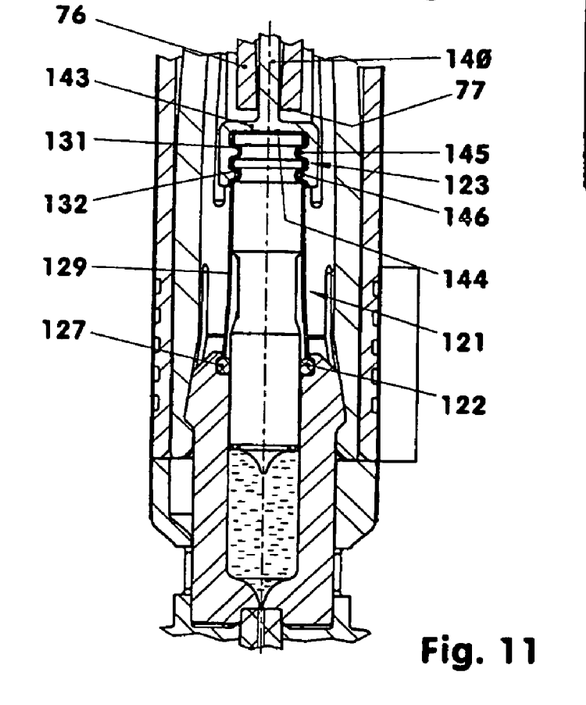
FIG. 11 shows the disposable injector with a finger-stall seal sealing the inner side of the cylinder and an encompassing pump rod.

FIG. 11 shows a sealing system (121) with a bellows-like sealing element (129), which reaches around the end face of the piston (111) like a finger stall. The cylinder-side fixing area (122) is part of an elastically deformable ring (127), which sits in an annular groove (116) of the cylinder inner wall (109). In the case of the illustrative embodiment shown in FIG. 10, with an extended piston (111), the sealing element (129) is not tensioned.

Here, the upper end of the piston has two circumferential flutes (131, 132) with, for example, an identical cross section. The pump rod (140) engages in the flutes (131, 132) with a locking adapter (143). The locking adapter (143) has elevations (145, 146) arranged on its inner surface, for example in the form of segments or circumferentially on two planes. The lower elevations (145) are, for example, flatter here than the upper ones, in order to make it easier for the locking adapter (143) to be pushed completely onto the piston (111) during assembly.

Optionally, the piston (111) may have only one flute (131; 132) and the locking adapter (143) only one plane of elevations (145; 146).

In the assembled state, the end face (144) of the locking adapter (143) may lie on the sealing element (129). Optionally, the locking adapter (143) may have axial play with respect to the piston (111) in the longitudinal direction of the disposable injector (4).

The transfer-pumping of the liquids takes place in the way described above. The pump rod (140), for example fixedly connected to the locking adapter (143), remains in the housing (10) after the transfer-pumping. If the pump rod (140) and the locking adapter (143) are connected to a coupling, the pump rod (140) may be removed after the transfer-pumping.

When the disposable injector (4) is triggered, the piston-actuating ram (60) strikes with the, for example planar, end face (77) of the piston slide (76) against the locking adapter (143), which, for example, by means of its end face (144), pushes the piston (111) forward to discharge the injection solution (3).

Figure 12:
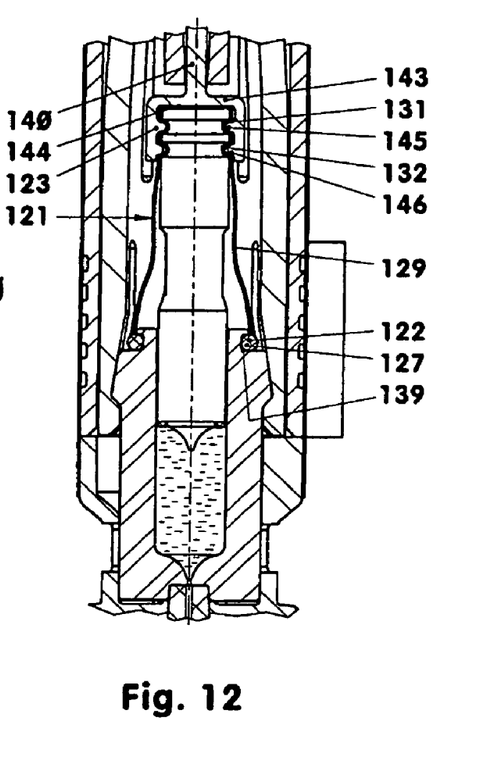
FIG. 12 shows a disposable injector with a finger-stall seal sealing the outer side of the cylinder and an encompassing piston rod.

The disposable injector (4) shown in FIG. 12 is of a similar construction to the illustrative embodiment shown in FIG. 11. The cylinder-side fixing area (123) of the one-part sealing system (121) is fastened on the outer side of the cylinder (101) in an annular groove (139). The sealing system (121) is fixed on the piston (111) by means of the locking adapter (143). The pump rod (140) is constructed in the way described in relation to FIG. 11. The transfer-pumping and triggering take place as in the previously described illustrative embodiment. After the triggering, the piston (111) moves quickly into its retracted stroke end position, the piston movement undergoing only very little frictional resistance.

The disposable injector (4) may be configured without a pump rod (140). For example, the second container (250) is then configured as the second cylinder-piston unit.

During the use of the illustrative embodiments shown in FIGS. 8-12, the sterility of the cylinder interior (110) is ensured even in the case of repeated transfer-pumping.

Combinations of the illustrative embodiments described are also conceivable.

LIST OF REFERENCE SIGNS 1 water for injection purposes, solvent
2 lyophilisate, active substance, medicament 3 injection solution
4 disposable injector, single-use injector
5 center line of the injector, longitudinal direction
6 triggering movement direction of (82), downward movement directional arrow
7 container pushing-in direction
9 surroundings
10 housing, one-part
13 outer surface, cylindrical, outer wall
19 spacer sleeve
21 pressure rods, support rods
22 cams
23 supporting surface
24 bearing surface
28 flexural beam
31 lateral area, lateral portion
33 apertures
39 base
41 fixing area for the cylinder-piston unit
42 spring hook
43 rear-engagement means
50 spring element, helical compression spring, spring energy store
57 flutes of (82)
59 inner wall of (82)
60 piston-actuating ram
62 guide pin
63 bore
73 ram plate
75 collar surface, conical
76 piston slide
77 end face
80 triggering unit
81 triggering cap
82 triggering element, triggering sleeve
83 widening
83 return flank
85 edge, sharp-edged
87 bore
90 tamper-evident seal, banderole, security element, adhesive label
92 edge part, rear; label part
93 edge part, front; label part
94 tear-off banderole
95 tear-off tab
99 twin-chamber system
100 cylinder-piston unit, first, injector-side
101 cylinder, injector-side
102 locking ring
103 end face
104 adhesive ring
105 chamber
106 bore, nozzle
107 recess in the end face
108 narrowed area
109 cylinder inner wall
110 cylinder interior
111 piston
112 annular groove
113 annular groove
114 sealing ring, seal
115 recess in (111)
116 annular groove in (109)
117 annular groove in (109)
118 sealed portion
119 widening of (111)
121 sealing system
122 fixing area, first fixing area
123 fixing area, second fixing area
124 sealing element
125 sealing element
126 bellows
127 elastically deformable ring
128 elastically deformable ring
129 bellows- or finger-stall-like sealing element
131 flutes
132 flutes
134 displacement space
135 compensating space
139 annular groove
140 pump rod
141 conical thread, angular thread
143 locking adapter
144 end face
145 elevations
146 elevations
148 scale
149 scale
200 container adapter
206 windows, on both sides
211 intermediate base
221 container area, container receptacle
223 locking elements, folding locking hooks, stops
224 locking elements, locking rear-engagement means
225 stops
230 cap
240 dual adapter
241 through-channel
245 container portion
250 container
253 opening
255 chamber, container interior
257 stopper, elastic, rubber stopper
258 flange edge
260 tear-off banderole
261 tear-off tab
262 perforation
265 valve hose

What is claimed is:

1. In combination with a disposable injector (4) having at least one cylinder-piston unit (100), the cylinder piston-unit (100) including a piston (111) and a cylinder (101) in operative arrangement, the piston (111) of which can move between two stroke end positions in relation to the cylinder (101), the cylinder-piston unit (100) comprising at least one sealing system (121) that seals a compensating space (135) from the surroundings (9), the improvement which comprises:
the piston (111) is provided at its front surface with an axial annular groove (112) for accommodating a seal ring (114) or a permanently elastic seal material,
the cylinder (101) carries a first seal element (127) and the piston (111) carries a second seal element (128, 131, 132) which is displaced with respect to the first by the piston stroke,
the first seal element (127) includes a first fixing area (122) and the second seal element (128, 131, 132) includes a second fixing area (123), the two fixing areas (122, 123) connected by means of a bellows (126) or by means of a bellows- or finger-stall-like sealing element (129).

2. The disposable injector (4) as claimed in claim 1, wherein it comprises a twin-chamber system (99).

3. The disposable injector (4) as claimed in claim 1, wherein the piston (111) protrudes from the cylinder (101) in the extended stroke end position.

4. The disposable injector (4) as claimed in claim 1, wherein the piston (111) further comprises a pump rod (140) operatively coupled to it.

5. The disposable injector (4) as claimed in claim 4, wherein the pump rod (140) further includes a locking adapter (143) formed on it, the locking adapter (143) surrounds the upper end of the piston (111) in the operative position.

6. The disposable injector (4) as claimed in claim 5, wherein the piston (111) has at least one circumferential flute (131, 132), the locking adapter (143) adapted to engage the at least one circumferential flute (131, 132) in the operative position.

7. The disposable injector (4) as claimed in claim 6, wherein the locking adapter (143) in the assembled state lies on a bellows- or finger-stall-like sealing element (129).

* * * * *